(12) United States Patent
Quintero et al.

(10) Patent No.: US 10,174,613 B2
(45) Date of Patent: Jan. 8, 2019

(54) EFFECTIVE POROSITY DETERMINATION FOR TIGHT GAS FORMATIONS

(71) Applicant: HALLIBURTON ENERGY SERVICES, INC., Houston, TX (US)

(72) Inventors: Luis F. Quintero, Katy, TX (US); Donald Westacott, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 283 days.

(21) Appl. No.: 15/104,509
(22) PCT Filed: Jan. 13, 2015
(86) PCT No.: PCT/US2015/011255
§ 371 (c)(1),
(2) Date: Jun. 14, 2016
(87) PCT Pub. No.: WO2015/108884
PCT Pub. Date: Jul. 23, 2015

(65) Prior Publication Data
US 2018/0163535 A1    Jun. 14, 2018

Related U.S. Application Data

(60) Provisional application No. 61/930,922, filed on Jan. 23, 2014, provisional application No. 61/927,048, filed on Jan. 14, 2014.

(51) Int. Cl.
*E21B 25/08*     (2006.01)
*E21B 49/06*     (2006.01)
(Continued)

(52) U.S. Cl.
CPC .............. *E21B 49/06* (2013.01); *E21B 25/08* (2013.01); *E21B 41/005* (2013.01); *E21B 43/16* (2013.01); *G01N 15/08* (2013.01); *G01N 33/241* (2013.01)

(58) Field of Classification Search
CPC .......... E21B 49/06; E21B 25/08; E21B 43/16; G01N 15/08
See application file for complete search history.

(56) References Cited

U.S. PATENT DOCUMENTS 4,573,342 A    3/1986  Stanley
4,627,270 A   12/1986  Stanley
(Continued)

FOREIGN PATENT DOCUMENTS

CN      102220865       4/2014
WO     2011/133885     10/2011
(Continued)

OTHER PUBLICATIONS

PCT International Search Report and Written Opinion, dated Apr. 29, 2015, Appl No. PCT/US2015/011248,"Tight Gas Formation Pressure Determination Method," Filed Jan. 13, 2015, 16 pgs.
(Continued)

*Primary Examiner* — Brad Harcourt
(74) *Attorney, Agent, or Firm* — Alan Bryson; Parker Justiss, P.C.

(57) ABSTRACT

A disclosed effective porosity determination method for tight gas formations includes: obtaining a core sample sealed in a pressure-maintaining core vault during transport out of the borehole; coupling the core vault to a collection chamber; based at least in part on measured pressure, temperature, and fluid volumes in the collection chamber, deriving the number of moles of gas retrieved with the core sample; and combining the number of moles with a downhole pressure, a downhole temperature, and a downhole core sample volume to determine an effective porosity of the tight gas formation. A system embodiment includes: a coring tool having a core vault with a seal to provide pressure-preserved transport of a core sample from a tight gas formation; a collection chamber that attaches to the core vault to measure volumes of fluids and gas; and a processing unit that responsively determines an effective porosity of the tight gas formation.

16 Claims, 8 Drawing Sheets

(51) Int. Cl.
*G01N 15/08* (2006.01)
*G01N 33/24* (2006.01)
*E21B 41/00* (2006.01)
*E21B 43/16* (2006.01)

(56) References Cited

U.S. PATENT DOCUMENTS 5,265,462 A * 11/1993 Blauch .................. G01N 15/08
73/38
2008/0083266 A1 4/2008 Gupta et al.
2010/0161229 A1* 6/2010 Georgi .................... G01V 9/00
702/11
2012/0152548 A1 6/2012 Hinkel et al.

FOREIGN PATENT DOCUMENTS

WO 2015/108880 7/2015
WO 2015/108884 7/2015

OTHER PUBLICATIONS

PCT International Search Report and Written Opinion, dated Appl No. PCT/US2015/011255, "Effective Porosity Determination for Tight Gas Formations," Filed Jan. 13, 2015, 14 pgs.
Espinal, Laura, "Porosity and its Measurement", Characterization of Materials, edited by Elton N. Kaufmann, Copyright 2012 John Wiley & Sons, Inc., 9 pgs.

* cited by examiner

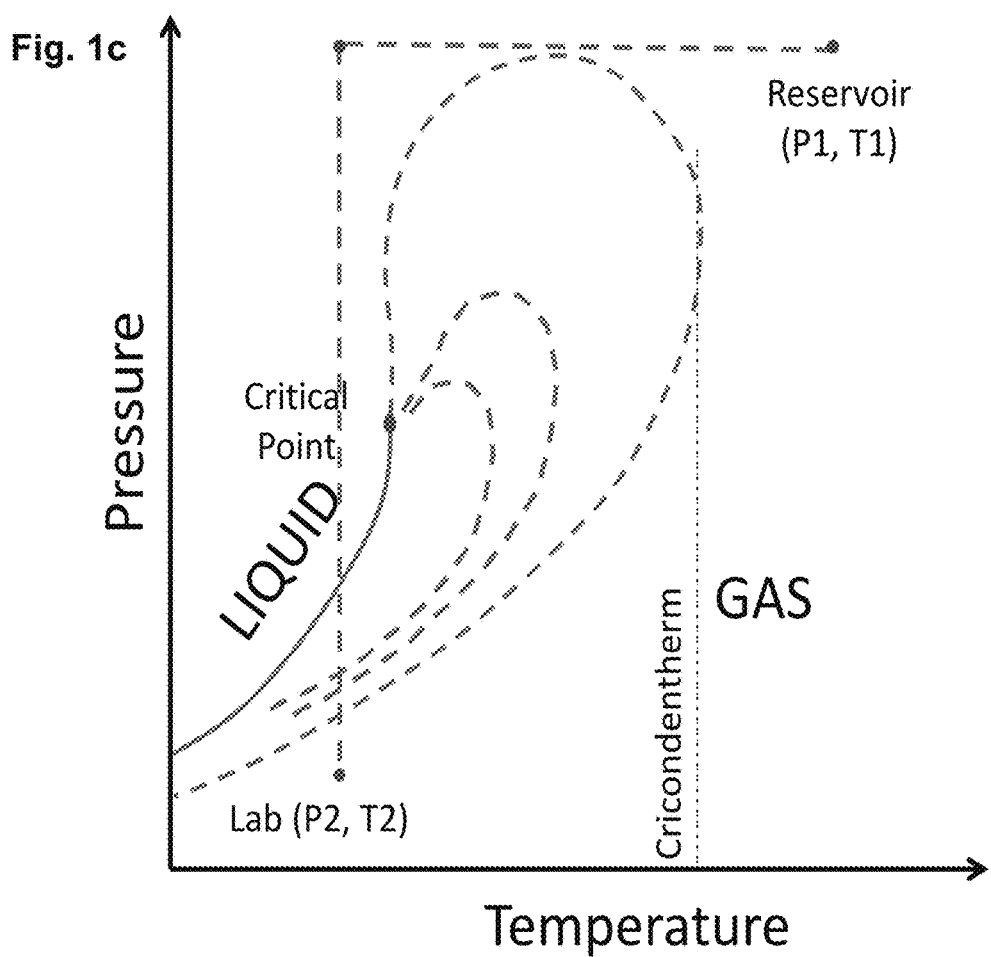

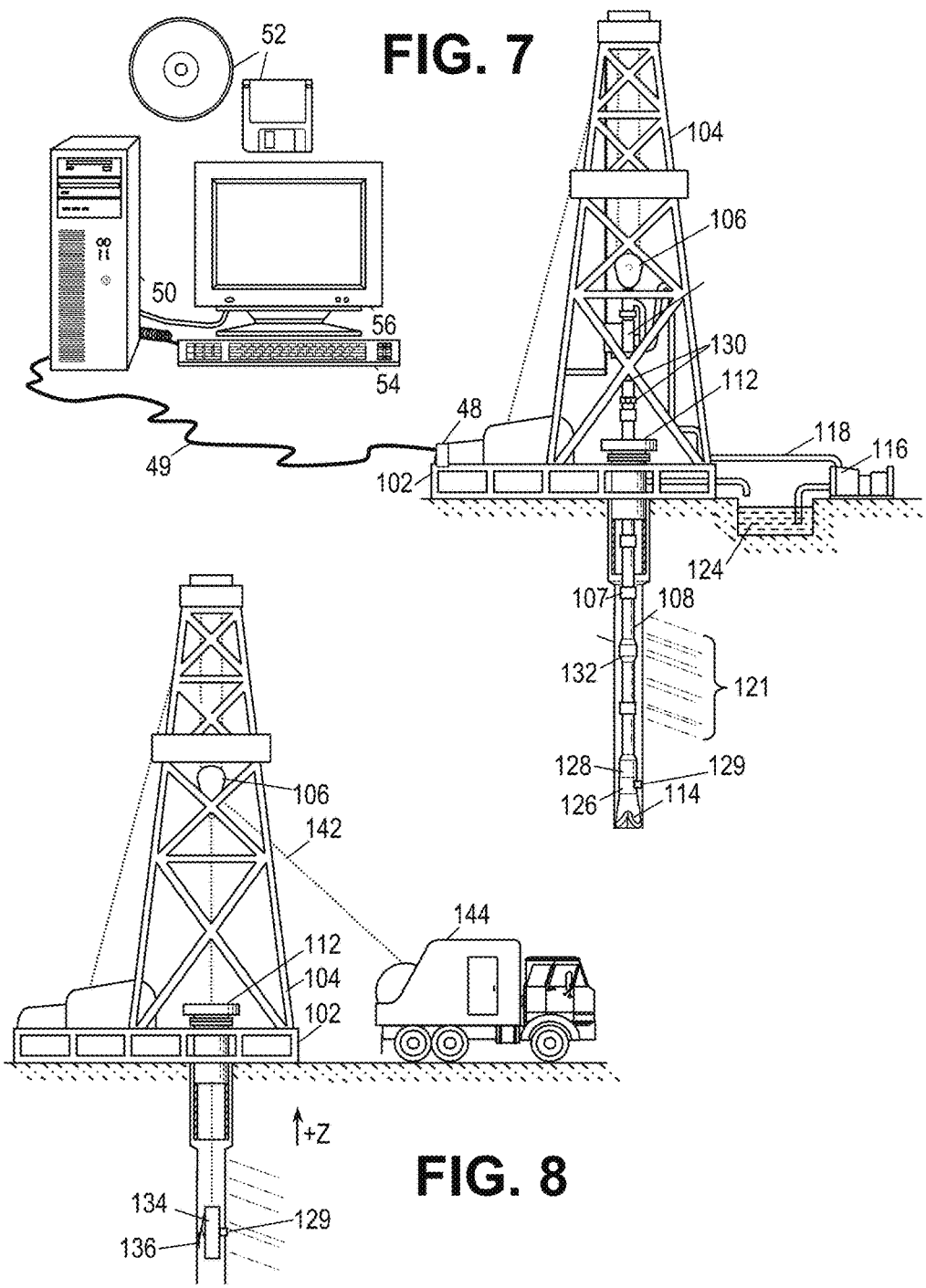

EFFECTIVE POROSITY DETERMINATION FOR TIGHT GAS FORMATIONS

CROSS-REFERENCE TO RELATED APPLICATIONS

The present application claims priority to U.S. Pat. App. 61/927,048, titled "Tight Gas Formation Pressure Determination Method", filed Jan. 14, 2014 by inventors Donald Westacott and Luis F. Quintero, and further claims priority to U.S. Pat. App. 61/930,922, titled "Effective Porosity Determination for Tight Gas Formations", filed. Jan. 23, 2014 by inventors Luis F. Quintero and Donald Westacott. Each of these applications is hereby incorporated herein by reference.

BACKGROUND

An important factor for managing the development and production of hydrocarbons from a subsurface formation is the effective porosity of the formation. Existing practices for determining effective porosity include a laboratory comparison of core density to the density of known matrix minerals saturated with a known fluid, with or without crushing or other destructive analysis of the core material to improve the mineralogy characterization; performing a mercury injection test and correlating capillary pressure to pore size; performing nuclear magnetic resonance (NMR)-based porosity measurement of the core; performing acoustic wave propagation-based porosity measurement of the core; and electrical conductivity-based porosity measurements of the core. However, when applied to tight gas formations, such practices can be inaccurate and unreliable due to fundamental assumptions about pore connectedness and in-situ properties of the fluids, which assumptions become more significant and unreliable as the porosity decreases.

Another existing approach, known as rate transient analysis (RTA) or dynamic data analysis (DDA), attempts to address this issue by applying the fundamental flow-pressure relationships to a much larger data set, i.e., the production data. These methods match the production curves (including responses to changing borehole conditions) to type curves for pre-existing reservoir models. While these methods appear to have some success, they unfortunately require a substantial amount of time to collect enough data points.

BRIEF DESCRIPTION OF THE DRAWINGS

Accordingly, there are disclosed in the drawings and detailed description specific embodiments of systems and methods providing effective porosity determination for tight gas formations. In the drawings:

FIGS. 1a-1c are illustrative P-T diagrams of a dry gas, respectively showing paths taken by a pressure-preserved core, a conventional core, and a pressure-preserved core after releasing the pressure.

FIG. 7 is an illustrative coring while drilling environment.

FIG. 8 is an illustrative wireline coring environment.

Figure 1A:
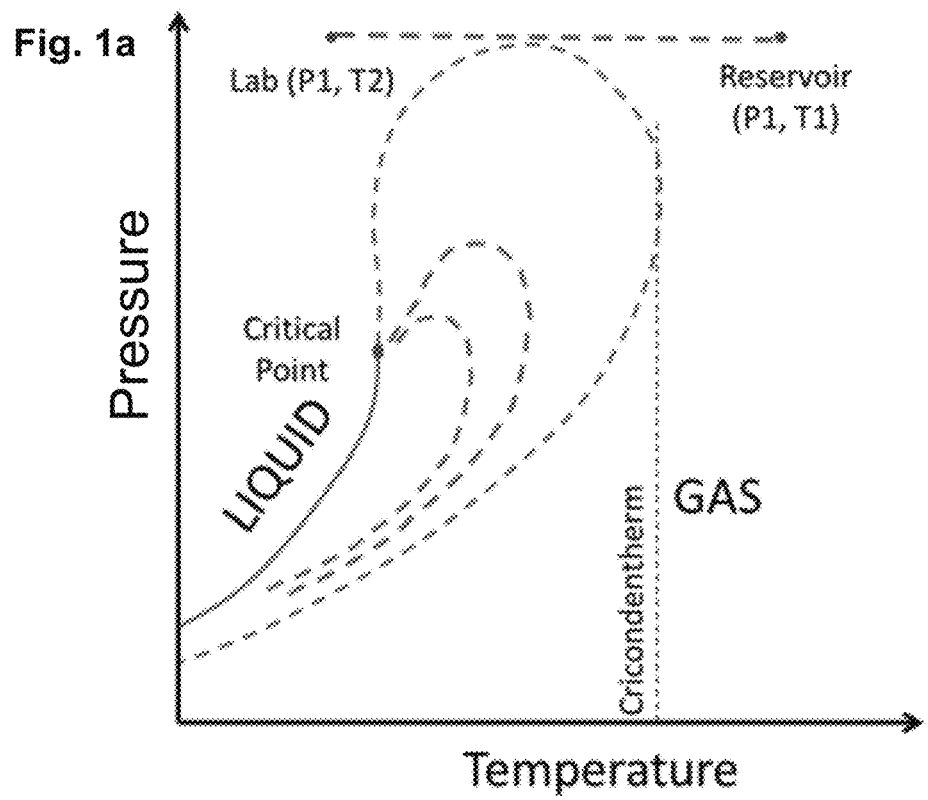

It should be understood, however, that the specific embodiments given in the drawings and detailed description do not limit the disclosure. On the contrary, they provide the foundation for one of ordinary skill to discern the alternative fours, equivalents, and modifications that are encompassed in the scope of the appended claims.

DETAILED DESCRIPTION

The following disclosure provides for a novel method, apparatus, and system for determining effective porosity ($\phi_e$) in gas-bearing tight formations through analysis at surface/lab conditions of pressure-preserved downhole core samples. The disclosed approach employs temperature and pressure measurements of the downhole formation, a core sample of the downhole formation, and the fundamental gas laws, $P_1V_1T_2=P_2V_2T_1$; $PV=ZnRT$, together with mixing laws for density of fluids, to calculate the effective porosity ($\phi_e$) of a gas-bearing tight formation.

Throughout the text, the suffix "0" denotes original conditions, "1" denotes coring conditions, and "2" denotes lab conditions. Primed subscripts 2' and 2" may be used to refer to different components of a quantity under lab conditions (e.g., different portions of a volume). References to effective porosity include both inter-grain and intra-grain porosity of the core sample. When multiplied by the volume of the core sample, the effective porosity provides the effective pore volume (also known as the "effective pore space") of the core sample.

Fundamental Concepts.

Reservoir conditions in a dry gas reservoir are such that the fluid is outside of the P-T envelope, and hence exist in a single phase. The reservoir temperature is presumed to be above the cricondentherm (maximum temperature above which liquid cannot be formed regardless of pressure), so that the in-situ reservoir fluid can only exist in a gaseous phase.

Figure 1B:
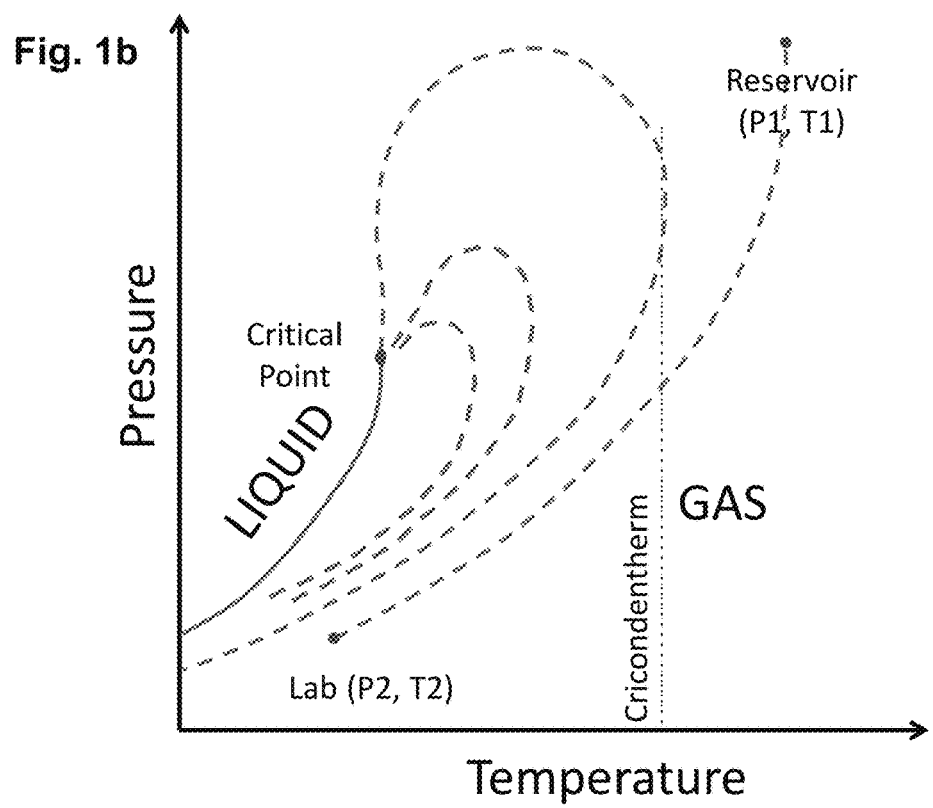

In the absence of liquids and with a rock of zero compressibility, gas trapped in a pressure-preserved core sample when brought from the reservoir to surface will only experience a change in temperature, as shown in FIG. 1a. In this scenario, all gas molecules are recovered in the core sample. For comparison, gas recovered in a conventional core sample will have followed a path as shown in FIG. 1b, typically with the reservoir fluid molecules escaping from the core sample en route to the surface.

Drilling and Coring: Hydrodynamics.

Figure 2A:
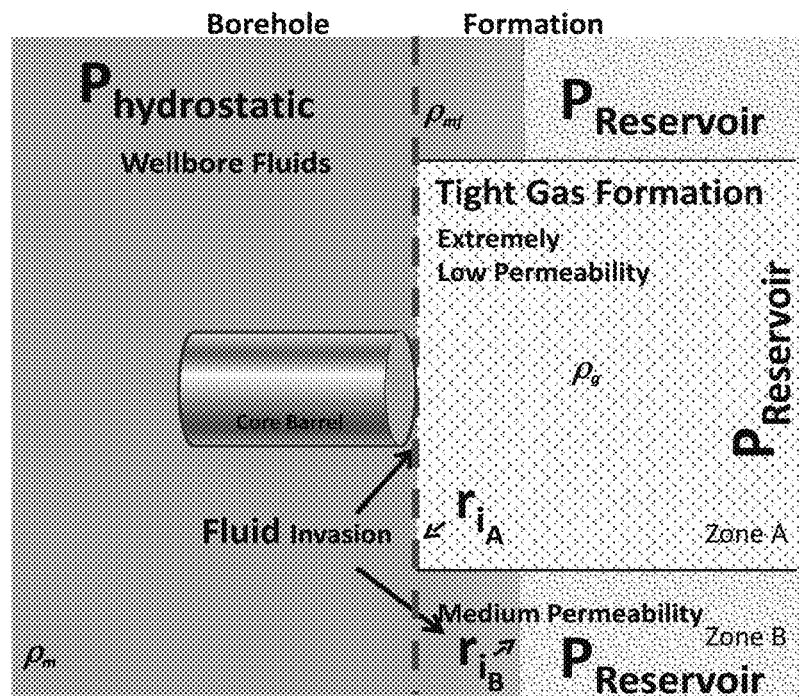
FIGS. 2a-2b are schematic pressure distribution maps before and after an illustrative coring operation.
Figure 2B:
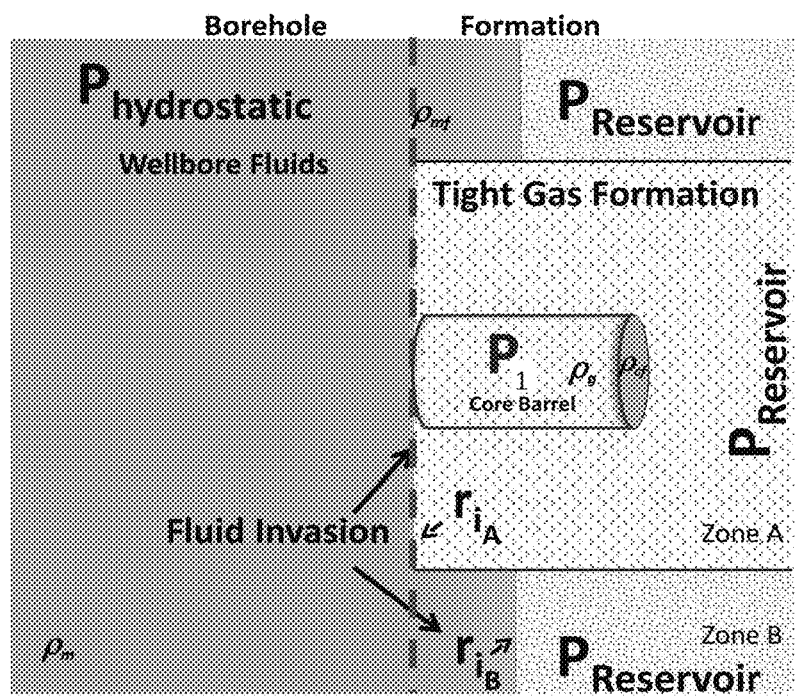

While drilling conventional formations, wellbore fluids (of density $\rho_m$) exert a hydrostatic pressure ($P_{hyd}$) which is greater than the reservoir pressure ($P_0$), and hence mud filtrate (of density $\rho_{mf}$) invades the formation up to a radius of invasion ($r_i$) as shown in FIG. 2a. (In FIGS. 2a and 2b, the radius of invasion for Zone A is labeled $r_{iA}$ and the radius of invasion for Zone B is labeled $r_{iB}$.) Mud additives quickly create a pseudo-impermeable layer (mudcake) that prevents the filtration process from continuing indefinitely. Hence the formation effective porosity ($\phi_e$) determines the ultimate radius of invasion for low to high permeability formations. Yet on a short time scale (the instantaneous or spurt-invasion process), it is the formation permeability (k) that controls the radius of invasion. In a tight gas formation where permeabilities are on the order of micro- and nano-darcies, the invasion is extremely shallow, e.g., on the order of minute fractions of an inch.

Similar fluid dynamics occur during coring operations, where a hollow coring bit cuts a cylindrical core sample from the side or bottom of a borehole. As the barrel of the coring bit presses a circle of cutting teeth against the formation to cut a circular trench around the core sample, the mud present in the borehole provides lubrication, but also transmits the hydrostatic pressure $P_{hyd}$ to the formation being exposed by the trench. In many cases this would tend to displace gas (of density $\rho_g$) deeper into the formation. However, since this disclosure deals with tight gas formations (i.e., formations having very low permeability) and the coring process generally requires only a few minutes to complete, the radius of invasion in the core sample is negligible. In other words, the mud filtrates only cover ("paint") the core sample without penetrating into it (see FIG. 2b). The foregoing should make it clear that when an extremely low permeability formation is cored, any gas displacement from the core sample is negligible.

Once the circular trench around the core sample has been cut to the desired depth (which is the desired length of the core sample), the core sample is separated from the formation, usually by rocking the bit or applying a sudden acceleration transverse to the axis of the coring bit to induce a shear fracture near the base of the core sample. Some alternative coring bit embodiments "grab" the base of the core sample and pull it free from the formation. In any event, the coring bit is then retracted from the formation with the core sample still positioned in the barrel of the coring bit.

Figure 3:
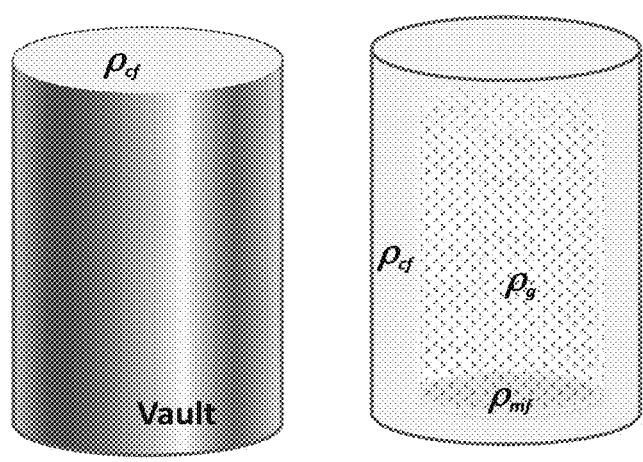
FIG. 3 shows schematic material distribution maps before and after an illustrative coring operation.

Conventional coring tool designs retrieve the coring tool to the surface with the core sample still held in the barrel of the coring bit. Some contemplated coring tool embodiments, however, displace the core sample from the barrel of the coring bit into a core vault, and seal the core vault to prevent the escape of any fluids or gases as the coring tool is retrieved to the surface. In particular, certain contemplated coring tool embodiments actively preserve the pressure inside the vault as the coring tool is retrieved to the surface, even as the tool undergoes a temperature decrease during transport. Such core samples are referred to herein as "pressure preserved core samples". In at least some coring tool embodiments, the core vault is initially filled with a high density coring fluid, $\rho_{cf}$ (e.g. sodium bromide), which is then displaced by the core sample as the core sample is inserted into the vault. Once the tool has placed the core sample in the core vault and sealed the vault (See FIG. 3), the fluids trapped in the core vault will be a mix of the "painted-on" mud filtrate, the coring fluid, the formation gas, and the irreducible water, which is treated here as part of the matrix. The total volume of producible fluids $V_f$ in the core vault is the volume of mud filtrate that has "painted" the core sample ($V_{mf}$), plus the volume of residual coring fluid ($V_{cf}$) and the volume of gas ($V_g$):

$$V_f = V_{mf} + V_{cf} + V_g \qquad \text{Eq. 1}$$

The total volume of the core vault is given by:

$$B = \pi r_B^2 L_B \qquad \text{Eq. 2}$$

where $r_B$ and $L_B$ refer to the internal radius and internal length of the core vault, respectively.

Since gas is presumed to remain trapped within the effective porosity of the core sample, $\varnothing_e$, during the coring operation, the volume of gas can be expressed as:

$$V_g = \varnothing_e C_1 \qquad \text{Eq. 3}$$

Where $C_1$ is the volume of the core sample. In a perfectly cylindrical core sample, $$V_g = \varnothing_e \pi r_{c1}^2 L_{c1} \qquad \text{Eq. 4}$$

where $$C_1 = \pi r_{c1}^2 L_{c1} \qquad \text{Eq. 5}$$

with $r_{c1}$ and $L_{c1}$ referring to the radius and length of the recovered core sample, respectively, at downhole (initial) conditions. The initial volume occupied by the core sample, $C_1$, is also $$C_1 = B - V_{mf1} + V_{cf1} \qquad \text{Eq. 6}$$

and $$B = C_1 + V_{mf1} + V_{cf1} \qquad \text{Eq. 7}$$

So that the volume of gas trapped inside the core sample during coring (initial conditions) is expressible as:

$$V_{g1} = \varnothing_e (B - V_{mf1} - V_{vcf1}) \qquad \text{Eq. 8}$$

Due to $P_{hyd}$, the pressure of the core sample ($P_1$) will be slightly larger than $P_0$, $$P_1 = P_0 + \Delta P_1 \qquad \text{Eq. 9}$$

and $$P_0 = P_1 - \Delta P_1 \qquad \text{Eq. 10}$$

Drilling and Coring: Thermodynamics

While drilling, wellbore fluids (at temperature $T_m$, which is measured) are in contact with the gas bearing formation which is at reservoir temperature ($T_0$, assumed to be known via wireline-logs or otherwise). Although the invasion is negligible in a tight gas formation, thereby reducing heat transfer through convection, heat transfer does continue through conduction.

Figure 4A:
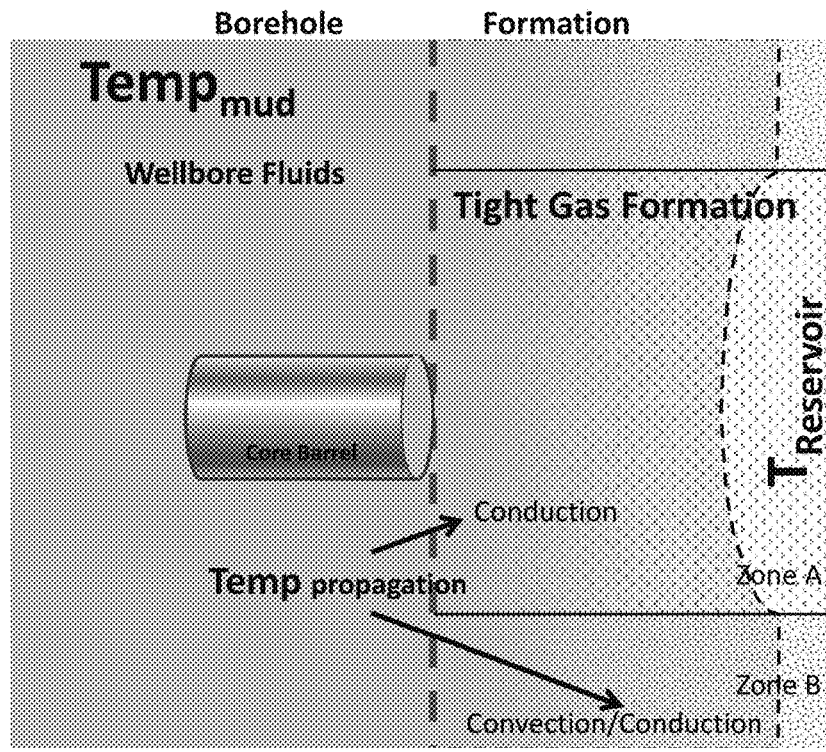
FIGS. 4a-4b are schematic temperature distribution maps before and after an illustrative coring operation.
Figure 4B:
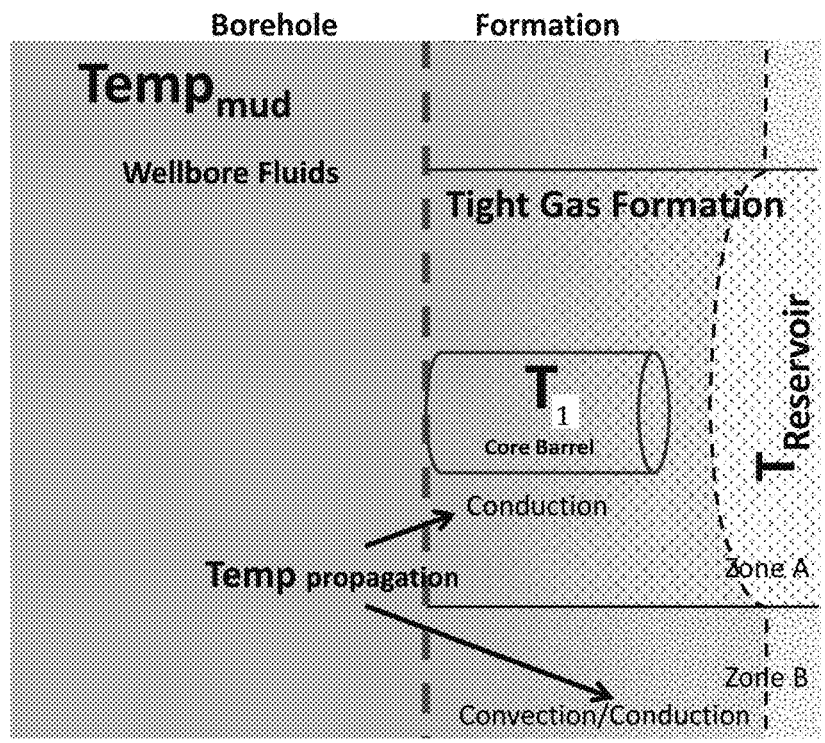

The actual temperature distribution along the wellbore while drilling will depend on several parameters, such as the temperature difference between $T_m$ and $T_0$, the heat coefficient of the formation and fluids. Inside the core vault, the heat coefficient of the vault, and coring fluid will also be of importance. Nevertheless, the mass of the core vault and coring fluid are extremely small compared to the overall mass of the drilling fluid, and therefore the temperature of the core sample can be assumed to depend only on $T_m$ and $T_0$. FIGS. 4a and 4b illustrate the temperature profile before and after coring.

In a pressure-preserved core sample, such as the one depicted in FIG. 4b, the temperature of the gas trapped inside the core sample ($T_1$) is bounded by $T_m$ and $T_0$.

$$T_1 = T_0 - \Delta T_1 \qquad \text{Eq. 11}$$

Drilling and Coring: Real Gas Law

The volume of gas inside the volume of rock to be cored, before coring ($V_{g0}$), follows the relationship:

$$P_0 V_{g0} = Z_0 n_0 R T_0 \qquad \text{Eq. 12}$$

Where $Z_0$ is the gas compressibility factor at original reservoir conditions of $P_0$ and $T_0$, R is the universal gas constant, and n is the amount of gas (moles) in the core sample. After coring, the volume of gas trapped inside the core sample follows the same equation.

$$P_1 V_{g1} = Z_1 n_1 R T_1 \qquad \text{Eq. 13}$$

Since we are considering a very tight formation, only an infinitesimal amount of gas molecules are displaced, and hence the number of moles in the core sample remains approximately the same.

$$n_1 \approx n_0 \quad \text{Eq. 14}$$

Solving for $V_{g1}$, $$V_{g1} = \frac{Z_1 n_1 R(T_0 - \Delta T_1)}{P_0 + \Delta P_1} \quad \text{Eq. 15}$$

and $$n_1 R = \frac{\phi_e(B - V_{mf1} - V_{cf1})(P_0 + \Delta P_1)}{Z_1(T_0 - \Delta T_1)} \quad \text{Eq. 16}$$

Releasing the Pressure

Figure 5:
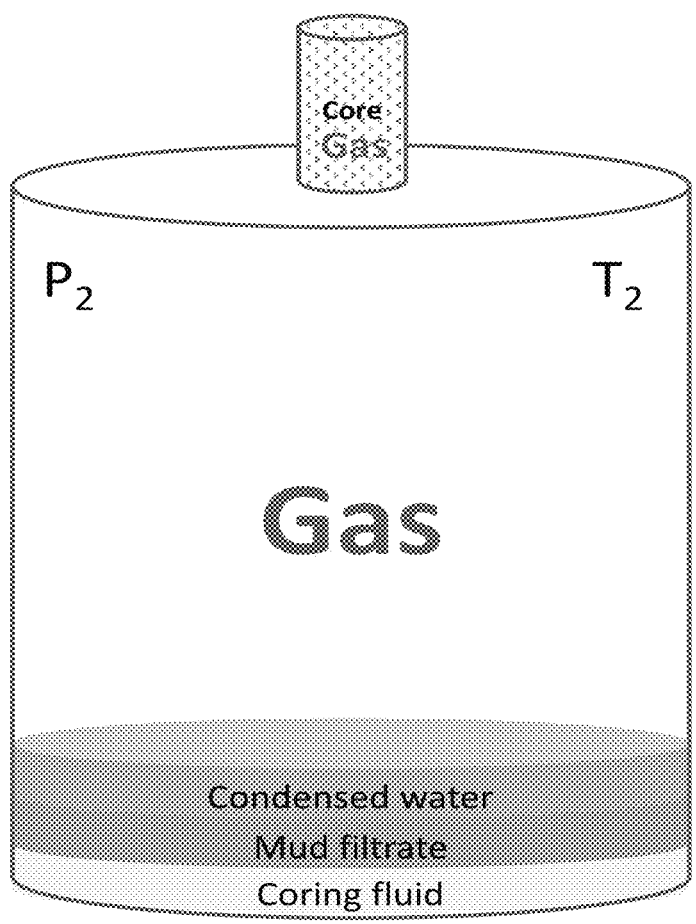
FIG. 5 is a schematic material distribution map in a collecting chamber.

When the pressured preserved core sample reaches the lab, a technician attaches the core vault to a collecting chamber via a sealed coupling as shown in FIG. 5. Initially, the collecting chamber is filled with a vacuum or an inert gas at a known temperature and pressure. The technician releases the seal on the core vault, gradually venting the pressure and fluids into the collecting chamber. The core may be retained in the core vault as fluids drain into the collection chamber. The collection chamber has a known volume $V_2$ and, once steady state has been reached, the collection chamber provides for the measurement of pressure, temperature, and volumes for each of the fluids. As the pressure is released into the collecting chamber, the fluid inside the core sample transits the path shown on FIG. 1c. Depending on lab conditions, the gas may have yielded little or no condensate, though if any condensate is present, its density can be calculated and used to determine the equivalent gas volume. Furthermore there may be some condensed water.

Therefore, the volume of fluids present in the collecting chamber ($V_{f2'}$) after the pressure has been reduced to $P_{2'}$ is given by the following expression:

$$V_{f2'} = V_{mf2} + V_{cf2} + V_w + V_{g2'} \quad \text{Eq. 17}$$

Since the net effect of pressure and temperature changes from reservoir to lab conditions results in a net gas expansion of several orders of magnitude, it is safe to assume that all the fluids that painted the core sample have been swept out of the core sample by gas, so that the only remaining fluid in the core vault is gas, except for capillary bound water (if any).

At equilibrium, the volume of gas still trapped in the core sample ($V_{g2''}$) will be equal to the effective core space $$V_{gC} = \phi_e C_2. \quad \text{Eq. 18}$$

where $C_2$ is the volume of the core sample under lab conditions. The core sample volume $C_2$ can be determined from physical measurements after the fluid measurements are complete and the core sample has been recovered from the core vault. Due to the change in pressure and temperature, the core sample volume $C_2$ may be different than the initial core sample volume downhole $C_1$. If desired, the compressibility and temperature coefficient of the core sample can be measured and used to estimate the downhole core sample volume $C_1$.

After the connection of the core vault to the collecting chamber, the total volume of fluids at lab conditions is also given by the volume of the chamber ($V_{ch}$) plus the empty space in the core vault (core vault minus the volume of the core sample) which is now occupied by gas ($V_{gB}$), plus the effective pore space of the core sample, $$V_{f2} = V_{ch} + (B - C_2) + \phi_e C_2 \quad \text{Eq. 19}$$

The total volume of gas in the collecting chamber, $V_{gch}$, is $$V_{gch} = V_{ch} - V_{mf2} - V_{cf2} - V_w \quad \text{Eq. 20}$$

The total volume of gas at lab conditions, $V_{g2}$, is:

$$V_{g2} = V_{gC} + V_{gch} + V_{gB}$$

And therefore, $$V_{g2} = V_{ch} - V_{mf2} - V_{cf2} - V_w + (B - C_2) + \phi_e C_2 \quad \text{Eq. 21}$$

Since $$V_{g2} = \frac{Z_2 n_2 R(T_2)}{P_2} \quad \text{Eq. 22}$$

$$n_2 R = \left[ \frac{V_{ch} - V_{mf2} - V_{cf2} - V_w + (B - C_2) + \phi_e C_2}{Z_2 T_2} \right] P_2 \quad \text{Eq. 23}$$

which represents the number of moles of gas in the lab.

Since the coring tool employed a sealed core vault to transport the pressure-preserved core sample, the number of moles in the lab and during coring is the same.

$$n_2 = n_1 \quad \text{Eq. 24}$$

Using the mud filtrate ($c_{mf}$) and coring fluid ($c_{cf}$) compressibilities $$V_{mf1} = V_{mf2}[1 - c_{mf}(P_2 - P_1)] \quad \text{Eq. 25}$$

and $$V_{cf1} = V_{cf2}[1 - c_{cf}(P_2 - P_1)] \quad \text{Eq. 26}$$

Recalling Eq. 16, it follows that $$\frac{\phi_e\{B - V_{mf1} - V_{cf1}\}P_1}{Z_1 T_1} = \left[ \frac{V_{ch} - V_{mf2} - V_{cf2} - V_w + (B - C_2) + \phi_e C_2}{Z_2 T_2} \right] P_2 \quad \text{Eq. 27}$$

$$\phi_e \{B - V_{mf1} - V_{cf1}\} \frac{P_1}{Z_1 T_1} = [V_{ch} - V_{mf2} - V_{cf2} - V_w + (B - C_2)] \frac{P_2}{Z_2 T_2} + \phi_e C_2 \frac{P_2}{Z_2 T_2} \quad \text{Eq. 28}$$

which can be solved for effective porosity:

$$\phi_e = \frac{[V_{ch} - V_{mf2} - V_{cf2} - V_w + (B - C_2)]\frac{P_2}{Z_2 T_2}}{\{B - V_{mf1} - V_{cf1}\}\frac{P_1}{Z_1 T_1} - C_2 \frac{P_2}{Z_2 T_2}} \quad \text{Eq. 29}$$

Since porosity has been assumed constant throughout this analysis, the original reservoir conditions can be substituted for the coring conditions. Using $C_0$ to represent the initial volume of the core sample at the reservoir temperature $T_0$ and pressure $P_0$, with a gas factor of $Z_0$:

$$\phi_e = \frac{[V_{ch} - V_{mf2} - V_{cf2} - V_w + (B - C_2)]\frac{P_2}{Z_2 T_2}}{C_0 \frac{P_0}{Z_0 T_0} - C_2 \frac{P_2}{Z_2 T_2}} \quad \text{Eq. 30}$$

Equation 29 (or 30) should be solved iteratively, since $$Z_1 = f(P_1) \quad \text{Eq 31}$$

$$V_{mf1} = f(P_1) \quad \text{Eq 32}$$

$$V_{cf1} = f(P_1) \quad \text{Eq 33}$$

Measurements

The following parameters can be measured with extreme accuracy at the lab: $V_{ch}$, $V_{mf2}$, $V_{cf2}$, $V_w$, B, $P_2$ and $T_2$. $T_m$ and $P_{hyd}$ can be measured downhole. An initial estimate of effective porosity $\phi_e$ can be estimated downhole via wireline logs, or in the lab. Reservoir pressure $P_0$ can be determined using hydrostatic extrapolation from nearby (more porous) formations where such pressure measurements are more reliable. Alternatively, the initial estimate of effective porosity can be combined with the laboratory measurements to obtain an estimated formation pressure. A very good approximation of $C_2$ ($C_{2th}$) can be measured or calculated. The compressibilities $c_{cf}$ and $c_{mf}$ can also be determined under laboratory and downhole conditions. The laboratory technician can analyze the gas in the collecting chamber to obtain the gas composition, molecular weight and density ($\rho_g$), so that $Z = f(P, T, \rho_g)$ can be determined, and with $P_2$ and $T_2$ determine $Z_2$.

There are a number of assumptions underlying this approach.

a) Since the permeability of the formation is very small, the time for coring is very short, core sample diameter is very small compared to the depth of the reservoir, $n_0 \approx n_1$ b) $T_0$ can be measured or determined independently, or, since the core sample is taken very close to the borehole face, estimated from $\Delta T_1 \approx 0 \rightarrow T_1 = T_m$.

c) $P_0$ can be measured or determined independently d) Since the formation is very tight, the effective porosity is the same downhole and at lab conditions.

Methodology

Figure 6:
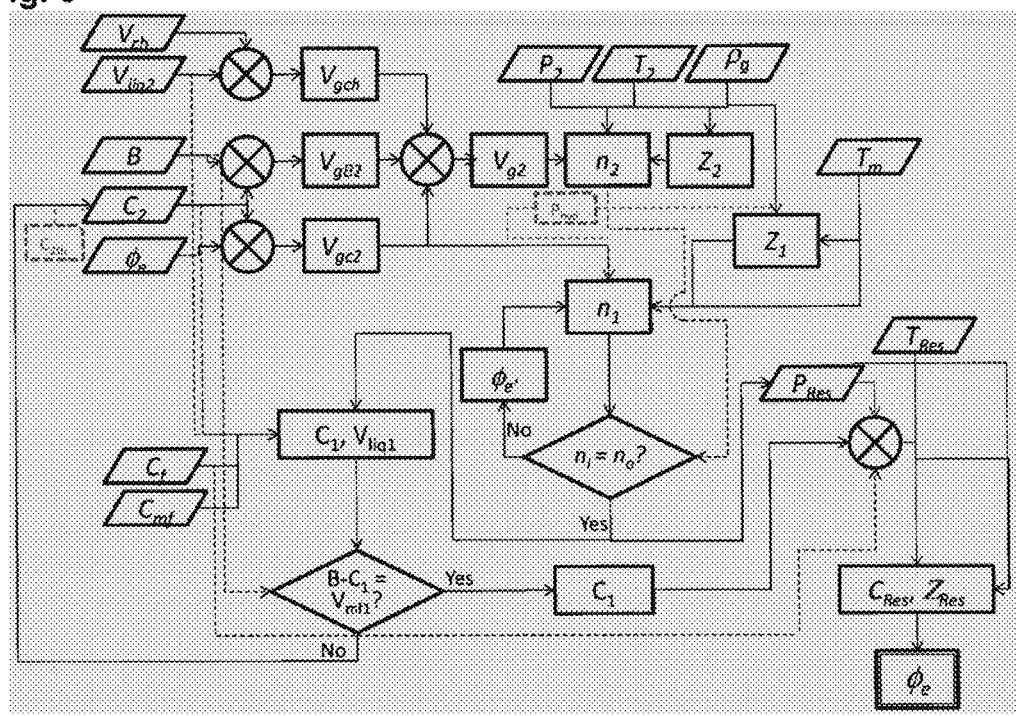
FIG. 6 is a data flow diagram of an illustrative method for effective porosity determination of tight gas formations.

FIG. 6 is a data flow diagram of an illustrative tight gas formation pressure determination method, which can be carried out with the following sequence of steps. It should be understood that the method can also be implemented with various steps performed in different order or in parallel.

1. Obtain a pressurized core sample from a tight gas formation
2. Keep the core sample in a vault or sealed barrel of known volume, B
3. Obtain from wireline-logs or another source an initial estimate of the effective porosity, $\phi_e$
4. Obtain from wireline-logs or other source the Reservoir Temperature, $T_0$
5. Estimate the reservoir pressure $P_0$, possibly from special core analysis.
6. Obtain from wireline-logs or other source the Mud Temperature during coring, $T_m$
7. Connect the Vault containing the core sample to a Collecting Chamber of known volume, $V_{ch}$
8. Allow the system reach equilibrium
9. Measure the Pressure of the system at lab conditions, $P_2$
10. Measure the Temperature of the system at lab conditions, $T_2$
11. Measure the Volume of Mud Filtrate collected in the Chamber, $V_{mf2}$
12. Obtain from tables or other source the Compressibility of the Mud Filtrate, $c_{mf}$
13. Measure the Volume of Coring Fluid collected in the Chamber, $V_{cf2}$
14. Obtain from tables or other source the Compressibility of the Coring Fluid, $c_{cf}$
15. Measure the Volume of condensed Water collected in the Chamber, $V_{w2}$
16. Obtain from tables or other source the Compressibility of the condensed Water, $c_w$ (Note: from this point onwards, and for simplification purposes only, the set of three liquid volumes $V_{mf2}$, $V_{cf2}$, $V_{w2}$ will be abbreviated as $V_{liq}$)
17. With the core sample dimensions, or by other means, calculate a theoretical value of Core Sample Volume, $C_{2th}$
18. Make the Core Sample Volume at lab conditions, $C_2$ equal to $C_{2th}$
19. Calculate the Volume of gas in the empty space of the vault, $V_{gB}$
20. Calculate the Volume of gas in the collecting Chamber, $V_{gch}$
21. Calculate the Volume of gas in the core sample, $V_{gC2}$
22. Add $V_{gB}$, $V_{gch}$, and $V_{gC}$ to obtain the total volume of gas at lab conditions, $V_{g2}$
23. Obtain through measurements or other source, the gas molecular weight or density, $\rho_g$
24. Obtain from correlations, tables or other source, the gas compressibility factor as a function of pressure, temperature and gas density, $Z = f(P, T, \rho_g)$
25. Using $P_2$, $T_2$ and $\rho_g$, calculate with $Z = f(P, T, \rho_g)$ or obtain through other methods, the gas compressibility factor at lab conditions, $Z_2$
26. Calculate using equation 23 or other method, the number of moles of gas corresponding to the lab volume of gas, $n_2$ (or some equivalent representation thereof, e.g., $n_2 R$)
27. Obtain from wireline-logs or other method the hydrostatic pressure of the wellbore while coring, $P_{hyd}$
28. Make the core sample pressure while coring, $P_1$ equal to $P_{hyd}$
29. Using, $P_i$, $T_m$ and $\rho_g$, calculate with $Z = f(P, T, \rho_g)$ or obtain through other methods, the gas compressibility factor at coring conditions, $Z_1$
30. With the volume of gas in the core sample at lab conditions, $V_{gC2}$, $P_1$, $T_m$ and $Z_1$, calculate using equation 10 the number of gas moles in the core sample during coring, $n_1$ (or some equivalent representation thereof, e.g., $n_1 R$)
31. Compare $n_1$ with $n_2$. If they are not equal, select a new value of $P_1$, and repeat steps 29 to 31 until the match is achieved. (Iteration 1)
32. Obtain from tables or other sources the Compressibility of the core sample material, $c_f$
33. With cf, $C_2$, $P_2$ and $P_i$, Calculate the volume of the Core sample at coring conditions, $C_1$
34. With $c_{liq}$, $V_{liq}$, $P_2$, and $P_i$, Calculate the volume of the liquids trapped in the vault at coring conditions,
35. Verify that the volume of liquids at coring conditions is identical to the difference between the vault volume, B, and the Core sample volume at coring conditions, $C_1$, If they are not equal, select a new value of $C_2$, and repeat steps 19 to 35 until the match is achieved (Iteration 2).

36. Multiply $C_1$ and $\phi_e$ to obtain the volume of gas in the core sample at coring conditions, $V_{gC1}$
37. The volume of the gas in the core during coring has been obtained.
38. Using $P_0$, $T_0$ and $\rho_g$, calculate with Z-f(P,T, $\rho_g$) or obtain through other methods, the gas compressibility factor at reservoir conditions, $Z_0$
39. With $V_{gC1}$, $P_0$, $T_0$ and $Z_1$, calculate using equation 12 the number of gas moles in the core sample at reservoir conditions, no (or some equivalent representation thereof, e.g., $n_0R$)
40. Solve for Reservoir effective porosity $\phi_e$ using equation 30.
41. The effective porosity of the core at reservoir conditions has been obtained.

The disclosed method enables the determination of an effective formation porosity $\phi_e$ in a safe, accurate, and relatively fast way. In part, it is safe because the time require to retrieve a pressurized core sample is measured in minutes, whereas the time required to do a welltest can be days or weeks. The likelihood of a tool getting stuck downhole are therefore greatly reduced. The accuracy results from the extremely small error ranges associated with each of the input variables, particularly those measurements being made under controlled laboratory conditions as opposed to downhole. The time required for a lab calculation of the fundamental properties of Z, $V_2$, $T_2$, $P_2$, is approximately one day. The final calculation can be made in minutes with a spreadsheet. (With the use of macros, the final calculation can be performed in less than a minute.)

FIG. 7 is an illustrative coring while drilling context for employing the above-disclosed principles. In the illustrated context, a drilling platform 102 is equipped with a derrick 104 that supports a hoist 106 for raising and lowering a drill string 108. The hoist 106 suspends a top drive 110 that rotates the drill string 108 as the drill string is lowered through the well head 112. The drill string 108 can be extended by temporarily anchoring the drill string at the well head 112 and using the hoist 106 to position and attach new drill pipe sections with threaded connectors 107.

Connected to the lower end of the drill string 108 is a drill bit 114. As bit 114 rotates, it creates a borehole 120 that passes through various formations 121. A pump 116 circulates drilling fluid through a supply pipe 118 to top drive 110, through the interior of drill string 108, through orifices in drill bit 114, back to the surface via the annulus around drill string 108, and into a retention pit 124. The drilling fluid transports cuttings from the borehole into the pit 124 and aids in maintaining the integrity of the borehole 120.

The drill bit 114 may be a coring bit for obtaining core samples from the bottom of the borehole. Alternatively, the bottom-hole assembly may include a sidewall coring tool 126 that can drive a coring bit 129 into the borehole wall to obtain a core sample. The bottom hole assembly may further include one or more logging tools 128 to acquire, e.g., downhole temperature and pressure measurements, as well as a log of effective porosity of the formation. Illustrative porosity logging tools include nuclear magnetic resonance (NMR) logging tools, neutron logging tools, and acoustic logging tools, and combinations thereof. The logging tool measurements may be stored in internal memory for retrieval when the bottom hole assembly returns to the surface, or may be communicated to the surface via mud pulse telemetry or another telemetry technique. A telemetry receiver array 130 may be coupled to tubing below the top drive 110 to receive transmitted telemetry signals. Many telemetry techniques also offer the ability to transfer commands from the surface to the bottomhole assembly, thereby enabling adjustment of the tool's configuration and operating parameters.

Telemetry receiver array 130 is coupled to an interface unit 48, which demodulates and digitizes the telemetry data. A wired or wireless connection 49 enables a computer 50 to receive the measurements of downhole temperature, pressure, effective porosity, and other parameters. Software (represented in FIG. 7 by non-transient information storage media 52) configures the computer 50 to provide a user interface which interact with a user via a keyboard or other input device 54 and a monitor or other output device 56. The user can instruct the computer to retrieve and process the appropriate log parameters and combine them with the laboratory measurements outlined above to determine an initial pressure of a tight gas formation.

At various times during the drilling process, the drill string 108 is removed from the borehole as shown in FIG. 8. Once the drill string has been removed, coring operations can be conducted using a wireline tool assembly 134 suspended in the borehole by a wireline cable 142. Wireline cable 142 has conductors for transporting power to the tool and telemetry from the tool to the surface. The wireline tool assembly 134 includes one or more logging instruments and a sidewall coring tool with a leveraging arm 136 that presses the tool against the opposite borehole wall as a coring bit 129 obtains a core sample. A logging facility 144 controls the various portions of the tool assembly 134, collecting measurements from the logging instruments and initiating operation of the coring bit 121 at one or more selected positions along the borehole. Logging facility 144 includes computing facilities for processing and storing the measurements gathered by the logging instruments. Such computing facilities can apply the principles outlined herein to determine tight gas formation pressures.

Figure 9:
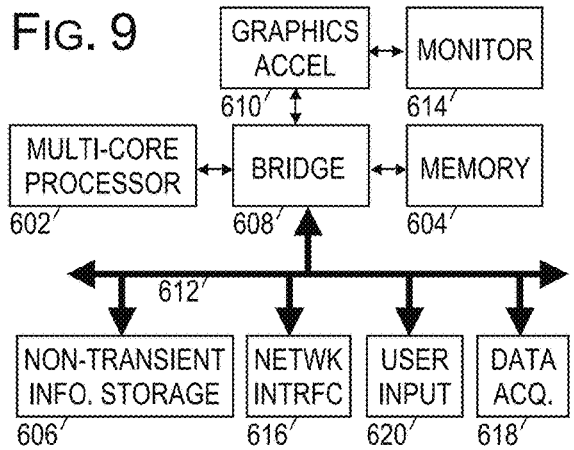
FIG. 9 is a block diagram of an illustrative pressure determination apparatus.

Computer 50 (FIG. 7), the logging facilities 144 (FIG. 8), or some other form of processing unit can be used to carry out the formation pressure determination methods outlined by the data flow diagram of FIG. 6 or the flow chart discussed below with respect to FIG. 10. FIG. 9 is a block diagram of one such illustrative processing unit. One or more multi-core processors 602 coordinate the operation of the unit based on software stored in memory 604 and/or in a non-transient information storage medium 606, such as a magnetic disk, an optical disk, or a flash drive. A bus bridge 608 couples the processor(s) 602 to memory 604, a graphics accelerator card 610, and to a bus 612 that enables the processor(s) 602 to access and control the rest of the system.

Graphics accelerator card 610 handles the primary support functions required by modern graphical user interfaces, enabling the processor(s) 602 to devote most of their computational capacity to less specialized tasks and simply forward the results to the graphics accelerator card 610 for display to a user via monitor 614. In addition to the non-transient information storage medium 606, the bus 612 enables the processor(s) to access other peripherals, including network interface cards 616, data acquisition cards 618, user input devices 620 (e.g., keyboards, pointing devices, cameras, microphones), and other input/output devices. Non-transient information storage medium 606 stores software that is loaded into memory 604 for execution by the processor 602 to carry out the disclosed methods. The software may include a basic operating system, spreadsheet software, and macros to carry out the disclosed methods. Alternative embodiments may employ custom software and data acquisition drivers to automate data acquisition and implementation of the disclosed methods.

Figure 10:
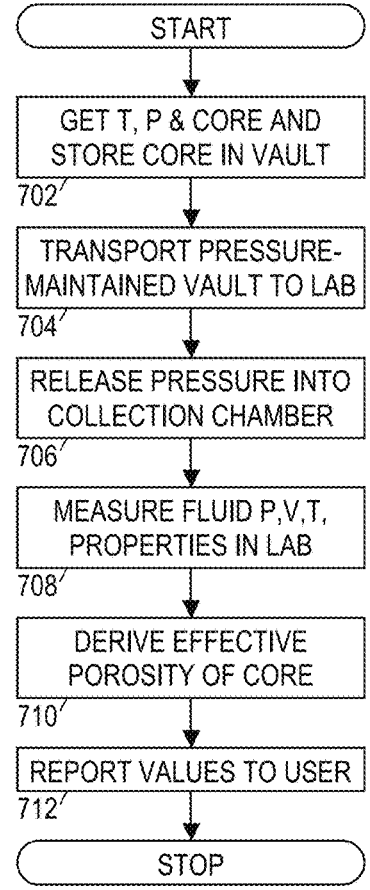
FIG. 10 is a flow chart of an illustrative pressure determination method.

In the illustrative method embodiment of FIG. 10, the downhole tool assembly measures the borehole temperature and pressure and obtains a core sample in block 702. The tool assembly stores the core sample in a core vault or seals the barrel of the coring bit to enable the pressure-preserved transport of the sample to a surface laboratory. The tool may further measure an initial estimate of the in-situ effective porosity of the formation. In block 704, the pressure-preserved core sample is transported to the lab. In block 706, a technician attaches the core vault or sealed coring bit barrel to an evacuated collection chamber and releases the fluids into the collection chamber. In block 708, after the collection chamber has reached steady state, the technician measures the temperature and pressure in the chamber, and further measures the volumes of the fluids (including the gas). The technician can further measure the composition of the gas and determine the compressibilities of each of the fluids, and can determine the volume of the core sample. Based on the various measurements, in block 710 a computer determines the effective porosity of the formation, and in block 712 the computer reports the formation pressure to a user, e.g. by displaying it on a monitor.

It is expected that the foregoing method will enable significantly improved modeling of fracturing operations in tight dry gas and/or dry shale gas formations, leading to improved production operations. It should further enable better forecasting of ultimate recoveries in such formations.

Accordingly, embodiments disclosed herein include:

A. A tight gas formation effective porosity determination method that comprises: obtaining a downhole core sample of a tight gas formation penetrated by a borehole, the core sample having been sealed in a pressure-maintaining core vault during transport out of the borehole; coupling the core vault to a collection chamber; based at least in part on measured pressure, temperature, and fluid volumes in the collection chamber, deriving the number of moles of gas retrieved with the core sample; and combining the number of moles together with a downhole pressure, a downhole temperature, and a downhole core sample volume to determine an effective porosity of the tight gas formation.

B. A tight gas formation effective porosity determination system that comprises: a coring tool having a core vault with a seal to provide pressure-preserved transport, the core vault receiving a core sample from a tight gas formation; a collection chamber that attaches to the core vault to receive and measure volumes of fluids and gas from the core sample; and a processing unit that, based at least in part on said volumes and a downhole pressure and a downhole temperature, determines an effective porosity of the tight gas formation.

C. A non-transient information storage medium having software that causes a processing unit carry out an effective porosity determination method for a tight gas formation, the method comprising: obtaining a temperature of the tight gas formation; obtaining a pressure of the tight gas formation; receiving pressure, volume, and temperature measurements of a gas in a collection chamber attached to a core vault having a pressure-preserved core sample from the tight gas formation; calculating the number of moles of gas retrieved with the core sample; combining the number of moles of gas together with the temperature and pressure of the tight gas formation and a downhole volume of the core sample to determine an effective porosity of the tight gas formation; and displaying the effective porosity.

Each of the embodiments A, B, and C may have one or more of the following additional elements in any combination: Element 1: the combining includes calculating a gas volume in the core sample during a coring operation. Element 2: the downhole temperature is a measured mud temperature during coring. Element 3: the downhole pressure is a hydrostatic borehole pressure during coring. Element 4: the combining further includes determining the effective porosity based at least in part on the gas volume, a reservoir temperature, and a reservoir pressure, while accounting for a compressibility of the gas volume and a compressibility of core sample material. Element 5: the reservoir temperature is obtained from a borehole temperature log. Element 6: the reservoir pressure is determined by measuring pressure of a formation more porous than the tight gas formation and performing hydrostatic extrapolation. Element 7: deriving the moles of gas includes determining a collection chamber gas volume and adding the collection chamber gas volume to the effective pore space of the core sample and to a core vault space around the core sample to obtain a total gas volume. Element 8: deriving the moles of gas includes (a) determining a gas compressibility based at least in part on a measured density or molecular weight of gas in the collection chamber; and (b) combining the compressibility with the total gas volume and equilibrium pressure and equilibrium temperature to get the number of moles of gas retrieved with the core sample. Element 9: the measuring of one or more liquid volumes in the collection chamber includes finding a volume and compressibility for each of: a mud filtrate, a coring fluid, and water. Element 10: the effective porosity is displayed. Element 11: the effective porosity is stored on a nonvolatile information storage medium for later display or processing.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A tight gas formation effective porosity determination method that comprises:
   obtaining a downhole core sample of a tight gas formation penetrated by a borehole, the core sample having been sealed in a pressure-maintaining core vault during transport out of the borehole;
   coupling the core vault to a collection chamber;
   based at least in part on measured pressure, temperature, and fluid volumes in the collection chamber, deriving a number of moles of gas retrieved with the core sample, wherein the deriving comprises:
   determining a gas volume of the collection chamber; and
   adding the collection chamber gas volume to an effective pore space of the core sample and to a space around the core sample in the core vault to obtain a total gas volume; and
   combining the number of moles together with a downhole pressure, a downhole temperature, and a downhole core sample volume to determine an effective porosity of the tight gas formation.

2. The method of claim 1, wherein the combining includes calculating a gas volume in the core sample during a coring operation.

3. The method of claim 2, wherein the downhole temperature is a measured mud temperature during coring, and the downhole pressure is a hydrostatic borehole pressure during coring.

4. The method of claim 2, wherein the combining further includes determining the effective porosity based at least in part on the gas volume, a reservoir temperature, and a reservoir pressure, while accounting for a compressibility of the gas volume and a compressibility of core sample material.

5. The method of claim 4, further comprising obtaining the reservoir temperature from a borehole log.

6. The method of claim 4, further comprising measuring pressure of a formation more porous than the tight gas formation and performing hydrostatic extrapolation to determine said reservoir pressure.

7. The method of claim 1, wherein the deriving further comprises:
   determining a gas compressibility based at least in part on a measured density or molecular weight of gas in the collection chamber; and
   combining the compressibility with the total gas volume and equilibrium pressure and equilibrium temperature to get the number of moles of gas retrieved with the core sample.

8. The method of claim 1, wherein measuring one or more liquid volumes includes finding a volume and compressibility for each of: a mud filtrate, a coring fluid, and water.

9. A tight gas formation effective porosity determination system that comprises:
   a coring tool having a core vault with a seal to provide pressure-preserved transport, the core vault receiving a core sample from a tight gas formation;
   a collection chamber that attaches to the core vault to receive and measure volumes of fluids and gas from the core sample; and
   a processing unit that, based at least in part on said volumes and a downhole pressure and a downhole temperature, determines an effective porosity of the tight gas formation, wherein:
      as part of determining the effective porosity, the processing unit calculates a gas volume in the core sample during a coring operation;
      as part of calculating the gas volume, the processing unit derives a number of moles of gas retrieved with the core sample; and
      as part of said deriving, the processing unit adds a gas volume of the collection chamber to an effective pore space of the core sample and to a space around the core sample in the core vault to obtain a total gas volume.

10. The system of claim 9, wherein the downhole temperature is a measured mud temperature during coring, and the downhole pressure is a hydrostatic borehole pressure during coring.

11. The system of claim 9, wherein the processing unit determines the effective porosity based at least in part on the gas volume, a reservoir temperature, and a reservoir pressure, while accounting for a compressibility of the gas volume and a compressibility of core sample material.

12. The system of claim 9, wherein as part of said deriving, the processing unit combines the total gas volume with a gas compressibility, a collection chamber temperature, and a collection chamber pressure.

13. A non-transient information storage medium having software that causes a processing unit carry out an effective porosity determination method for a tight gas formation, the method comprising:
   obtaining, by a logging tool, a temperature of the tight gas formation;
   obtaining, by the logging tool, a pressure of the tight gas formation;
   receiving, by the processing unit, pressure, volume, and temperature measurements of a gas in a collection chamber attached to a core vault having a pressure-preserved core sample from the tight gas formation;
   calculating, by the processing unit, a number of moles of gas retrieved with the core sample, wherein the calculation of the number of moles comprises:
      determining a gas volume of the collection chamber; and
      adding the collection chamber gas volume to an effective pore space of the core sample and to a space around the core sample in the core vault to obtain a total gas volume;
   combining, by the processing unit, the number of moles of gas together with the temperature and pressure of the tight gas formation and a downhole volume of the core sample to determine an effective porosity of the tight gas formation; and
   displaying on a display, by the processing unit, the effective porosity.

14. The medium of claim 13, wherein as part of said determining, the method carried out by the processing unit includes calculating a gas volume in the core sample during a coring operation.

15. The medium of claim 14, wherein the downhole temperature is a measured mud temperature during coring, and the downhole pressure is a hydrostatic borehole pressure during coring.

16. The medium of claim 14, wherein the method carried out by the processing unit includes determining the effective porosity based at least in part on the gas volume, a reservoir temperature, and a reservoir pressure, while accounting for a compressibility of the gas volume and a compressibility of core sample material.

* * * * *

UNITED STATES PATENT AND TRADEMARK OFFICE
CERTIFICATE OF CORRECTION

PATENT NO. : 10,174,613 B2
APPLICATION NO. : 15/104509
DATED : January 8, 2019
INVENTOR(S) : Luis F. Quintero and Donald Westacott It is certified that error appears in the above-identified patent and that said Letters Patent is hereby corrected as shown below:

In the Specification

In Column 2, Line 10, delete "fours," and insert --forms,--

In Column 4, Line 25, after --larger than-- delete "$P_o$," and insert --$P_0$,--

In Column 4, Line 27 approximately, delete "$P_1 = P_o + \Delta P_1$" and insert --$P_1 = P_0 + \Delta P_1$--

In Column 4, Line 31, delete "$P_o = P_1 - \Delta P_1$" and insert --$P_0 = P_1 - \Delta P_1$--

In Column 4, Line 35, delete "$T_o$," and insert --$T_0$,--

In Column 4, Line 40, delete "$T_o$," and insert --$T_0$,--

In Column 4, Line 49, delete "$T_o$." and insert --$T_0$.--

In Column 4, Line 53, delete "$T_o$." and insert --$T_0$.--

In Column 4, Line 55, delete "$T_1 = T_o - \Delta T_1$" and insert --$T_1 = T_0 - \Delta T_1$--

In Column 4, Line 58, after --coring-- delete "$(V_{go})$," and insert --$(V_{g0})$,--

In Column 4, Line 60, delete "$P_o V_{go} = Z_o n_o R T_o$" and insert --$P_0 V_{g0} = Z_0 n_0 R T_0$--

In Column 4, Line 61, after --Where-- delete "$Z_o$" and insert --$Z_0$--

In Column 4, Line 62, after --conditions of-- delete "$P_o$ and $T_o$," and insert --$P_0$ and $T_0$,--

In Column 5, Line 5 approximately, delete "$n_1 \approx n_o$" and insert --$n_1 \approx n_0$--

Signed and Sealed this
Second Day of April, 2019

Andrei Iancu
*Director of the United States Patent and Trademark Office*

CERTIFICATE OF CORRECTION (continued)
U.S. Pat. No. 10,174,613 B2

In Column 6, Line 65, after --Using-- delete "$C_o$" and insert --$C_0$--

In Column 6, Line 66, after --temperature-- delete "$T_o$" and insert --$T_0$--

In Column 6, Line 67, after --and pressure-- delete "$P_O$ , with a gas factor of $Z_O$:" and insert --$P_0$, with a gas factor of $Z_0$:--

In Column 7, Line 19, after --Reservoir pressure-- delete "$P_o$" and insert --$P_0$--

In Column 7, Line 37, delete "$n_o \approx n_1$" and insert --$n_0 \approx n_1$--

In Column 7, Line 41, delete "$P_o$" and insert --$P_0$--

In Column 7, Line 57, delete "$T_o$" and insert --$T_0$--

In Column 7, Line 57, after --pressure-- delete "$P_o$" and insert --$P_0$--

In Column 8, Line 45, delete "Using, $P_i$," and insert --Using $P_1$,--

In Column 8, Line 62, after --conditions-- insert --$V_{liq1}$--

In Column 9, Line 5, delete "Using $P_O$, $T_O$ and $\rho_g$, calculate with Z-f(P,T, $\rho_g$)" and insert --Using $P_0$, $T_0$ and $\rho_g$, calculate with $Z = f(P,T, \rho_g)$--

In Column 9, Line 7, after --conditions,-- delete "$Z_o$" and insert --$Z_0$--

In Column 9, Line 11, after --thereof, e.g.,-- delete "$n_oR$)" and insert --$n_0R$)--